(12) United States Patent
Tabata et al.

(10) Patent No.: US 10,765,110 B2
(45) Date of Patent: Sep. 8, 2020

(54) AGENT FOR PRESERVING BIOLOGICAL COMPONENT

(71) Applicants: Yasuhiko Tabata, Kyoto (JP); Denka Company Limited, Tokyo (JP)

(72) Inventors: Yasuhiko Tabata, Kyoto (JP); Kenji Fujii, Tokyo (JP); Masamichi Hashimoto, Tokyo (JP); Akio Ohno, Tokyo (JP)

(73) Assignees: Yasuhiko Tabata, Kyoto (JP); Denka Company Limited, Tokyo (JP)

(*) Notice: Subject to any disclaimer, the term of this patent is extended or adjusted under 35 U.S.C. 154(b) by 17 days.

(21) Appl. No.: 15/524,057

(22) PCT Filed: Nov. 10, 2015

(86) PCT No.: PCT/JP2015/081622
§ 371 (c)(1),
(2) Date: May 3, 2017

(87) PCT Pub. No.: WO2016/076317
PCT Pub. Date: May 19, 2016

(65) Prior Publication Data
US 2017/0311586 A1 Nov. 2, 2017

(30) Foreign Application Priority Data
Nov. 11, 2014 (JP) ................. 2014-228999

(51) Int. Cl.
*A01N 1/02* (2006.01)
*C12N 1/04* (2006.01)
*C12N 5/00* (2006.01)

(52) U.S. Cl.
CPC ........... *A01N 1/021* (2013.01); *A01N 1/0231* (2013.01); *C12N 1/04* (2013.01); *C12N 5/00* (2013.01)

(58) Field of Classification Search
CPC ........ A01N 1/021; A01N 1/0231; C12N 1/04; C12N 5/00
USPC ......................................................... 435/1.3
See application file for complete search history.

(56) References Cited

U.S. PATENT DOCUMENTS 8,361,484 B2 * 1/2013 Ingenito ............... A61K 31/736
424/400

FOREIGN PATENT DOCUMENTS

| EP | 2727597 A1 | 5/2014 |
|---|---|---|
| JP | H06-040801 A | 2/1994 |
| JP | H06-107538 A | 4/1994 |
| JP | 2002-218697 A | 8/2002 |
| JP | 2006-230396 A | 9/2006 |
| JP | 2006-306821 A | 11/2006 |
| JP | 2012-036131 A | 2/2012 |
| WO | WO 2013/159757 A1 | 10/2013 |
| WO | WO 2014/110454 * 7/2014 | ............... C08L 5/08 |

OTHER PUBLICATIONS

Kodavaty et al., Mechanical and Swelling Properties of Poly (vinyl alcohol) and Hyaluronic Acid Gels used in Biomaterial Systems—a Comparative Study, Defence Science Journal, vol. 64, No. 3, May 2014, pp. 222-229.*
Hare et al., Preparation of Polyvinyl Alcohol Hydrogel Through the Selective Complexation of Amorphous Phase, Journal of Applied Polymer Science, vol. 82, Iss. 1, (2001), pp. 143-149.*
Bae et al., "Nonfrozen Preservation of Articular Cartilage by Epigallocatechin-3-Gallate Reversibly Regulating Cell Cycle and NF-κB Expression", *Tissue Engineering, Part (A)*, 16: 595-603 (2010).
Gerecht et al., "Hyaluronic acid hydrogel for controlled self-renewal and differentiation of human embryonic stem cells", *PNAS*, 104(27): 11298-11303 (2007).
Guan et al., "Boronic acid-containing hydrogels: synthesis and their applications", *Chemical Society Reviews*, 42:8106-8121 (2013).
Konno et al., "Temporal and spatially controllable cell encapsulation using a water-soluble phospholipid polymer with phenylboronic acid moiety", *Biomaterials*, 28: 1770-1777 (2007).
Kurematsu, "Experimental Handbook for Cultured Cells", *Yudosha Co., Ltd.*, 69-74 (2004).
Liu et al., "Modified Hyaluronan Hydrogels Support the Maintenance of Mouse Embryonic Stem Cells and Human Induced Pluripotent Stem Cells", *Macromolecular Bioscience*, 12(8): 1034-1042 (2012).
Mohand-Kaci et al., "Optimized Hyaluronic Acid-Hydrogel Design and Culture Conditions for Preservation of Mesenchymal Stem Cell Properties", *Tissue Engineering, Part C*, 19(4): 288-297 (2013).
Squifflet et al., "Safe preservation of human renal cadaver transplants by Euro-Collins solution up to 50 hours", *Transplantation proceedings*, 13(1): 693-696 (1981).
Tarus et al., "Readily Prepared Dynamic Hydrogels by Combining Phenyl Boronic Acid- and Maltose-Modified Anionic Polysaccharides at Neutral pH", *Macromolecular Rapid Communications*, 35(24): 2089-2095 (2014).
Thorne et al., "Microgel applications and commercial considerations", *Colloid and Polymer Science*, 289: 625-646 (2011).
Wahlberg et al., "72-Hour preservation of the canine pancreas", *Transplantation articles*, 43: 5-8 (1987).
Wu et al., "Phenylboronic acid grafted chitosan as a glucose-sensitive vehicle for controlled insulin release", *Journal of Pharmaceutical Sciences*, 100(6): 2278-2286 (2011).
Japan Patent Office, International Search Report issued in International Application No. PCT/JP2015/081622 (dated Feb. 16, 2016) 2 pp.

(Continued)

Primary Examiner — Jennifer M. H. Tichy
(74) Attorney, Agent, or Firm — Leydig, Voit & Mayer, Ltd.

(57) ABSTRACT

Provided is an agent for preserving a biological component, comprising a hydrogel, the hydrogel comprising a crosslinked product formed from a compound having a plurality of hydroxyl groups and a modified hyaluronic acid having substituents capable of reacting with the hydroxyl groups to form a crosslinked structure.

4 Claims, 4 Drawing Sheets

(56) References Cited

OTHER PUBLICATIONS

Japan Patent Office, Written Opinion issued in International Application No. PCT/JP2015/081622 (dated Feb. 16, 2016) 5 pp.
International Bureau of WIPO, International Preliminary Report of Patentability issued in International Application No. PCT/JP2015/081622 (dated May 26, 2017) 2 pp.

* cited by examiner

AGENT FOR PRESERVING BIOLOGICAL COMPONENT

CROSS-REFERENCE TO RELATED APPLICATIONS

This patent application is the U.S. national phase of International Application No. PCT/JP2015/081622, filed on Nov. 10, 2015, which claims the benefit of Japanese Patent Application No. 2014-228999, filed Nov. 11, 2014, the disclosures of which are incorporated herein by reference in their entireties for all purposes.

TECHNICAL FIELD

The present invention relates to an agent for preserving a biological component and a method for recovering a biological component. The present invention also relates to a hydrogel suitable as a preserving agent, a modified hyaluronic acid capable of being suitably used in the preserving agent, and a kit for providing the preserving agent. The present invention further relates to a mixture comprising a biological component and a hydrogel.

BACKGROUND ART

Typically, as a method for preserving a biological component (for example, animal cells), there is a method which involves dispersing cells in a freeze preservative liquid, placing the resulting liquid in a tube for freeze preservation, and freeze-preserving the liquid in the tube (for example, Non Patent Literature 1). The major freeze preservative liquids to be used include a liquid obtained by adding 10% dimethyl sulfoxide into a culture medium or serum, and commercially available ones. A techniques have been also studied for holding and preserving frozen cultured cells in a culture vessel (Patent Literature 1).

Techniques for chilled preservation have been also studied. For example, Euro-Collins liquid (Non-Patent Literature 2), UW liquid (University of Wisconsin liquid) (Non Patent Literature 3), ET-kyoto liquid (Patent Literature 2), and the like have been known as a cell/tissue-preservation liquid for chilled preservation, which have been conventionally used. Patent Literature 3 describes a preservation solution for eyeball to be used for corneal transplantation that contains hyaluronic acid or its salt.

ThelioKeep, CPS-1, and the like are marketed as a commercial chilled preservation liquid. ThelioKeep contains catechin as an active ingredient and is applied to the preservation of tissues, particularly epithelial and endothelial skins and nerve tissues (Non Patent Literature 4 and Patent Literature 4). CPS-1, in which the composition of salts is optimized, is a reagent tailored for floating cells (Patent Literature 5).

A method for preserving cells, focusing attention on phosphorylcholine as a phospholipid constituting the cell membrane has been also reported (Non Patent Literature 5).

In addition, HyStem (trademark) has recently been commercially available, which is a modified hyaluronic acid for subjecting cells to 3-dimensional embedding culture (Non Patent Literatures 6, 7, and 8).

Meanwhile, Non Patent Literature 9 discloses the use of a hydrogel using phenylboronic acid-modified chitosan in the field related to diabetes treatment. Patent Literature 6 discloses a technique for using a hydrogel using phenylboronic acid-modified hyaluronic acid together with a therapeutic agent for diabetes in the field of the drug delivery system.

CITATION LIST

Patent Literature

Patent Literature 1: JP 2002-218967 A
Patent Literature 2: JPH6-40801 A
Patent Literature 3: JPH6-107538 A
Patent Literature 4: JP 2006-306821 A
Patent Literature 5: JP 2006-230396 A
Patent Literature 6: EP 2727597 A1

Non Patent Literature

Non Patent Literature 1: "Experimental Handbook for Cultured Cells", p. 69-74, 2004, Yodosha Co., Ltd
Non Patent Literature 2: Transplant Proc., 13, 693, 1981
Non Patent Literature 3: Transplantation, 43, 5, 1987
Non Patent Literature 4: Tissue Engineering: Part A 16 (2010) 595-603
Non Patent Literature 5: Biomaterials 28 (2007) 1770-1777
Non Patent Literature 6: PNAS (2007) vol. 104, No. 27, 11298-11303
Non Patent Literature 7: Macromol. Biosci. (2012) vol. 12, 1034-1042
Non Patent Literature 8: Tissue Engineering: Part C (2013) vol. 19 No. 4, 288-297
Non Patent Literature 9: Journal of Pharmaceutical Sciences (2011) vol. 100, No. 6, 2278-2286

SUMMARY OF INVENTION

Technical Problem

With the recent progress of regenerative medicine, the importance of technology has increased for transporting a biological component between various institutions, such as a medical institution, a research institution, and the cell-processing plant. As methods for preservation in transporting a biological component, freeze preservation and chilled preservation are used.

However, freeze preservation takes several days to properly freeze a biological component and also requires proper transport using dedicated freezing equipment. For freeze preservation, particularly, cells having high research/clinical significance, such as a primary cell culture, germ cells, fused cells, and gene-introduced cells are difficult to preserve by freezing even under strict temperature control. In addition, freeze preservation has problems of, for example, concern for the decomposition/denaturation of protein, which promotes the induction of differentiation of undifferentiated cells, including hepatocytes, such as ES cells and iPS cells.

For chilled preservation, there are a case where cells are transported in a state adhered to a culture dish and a case where cells are transported in a state dispersed in a preservation liquid. However, the former case has the following problems: damage due to oscillation is significant, and only the amount of cells on the culture dish surface can be transported. In the latter case, cells are damaged by oscillation, and in addition, settled cells adhere to one another to form cell mass, which lead to concern for, for example, cell death and differentiation induction promotion.

To avoid the damage due to oscillation, Non Patent Literatures 6 to 8 disclose methods involving embedding biological components using a hydrogel. However, the use of the hydrogel described in Non Patent Literatures 6 to 8 (HyStem (trademark)) has the problem of taking long time to recover biological components because of requiring the dissolution of the hydrogel with hyaluronidase for the recovery, and also has concern, for example, for the contamination of the degrading enzyme into the biological components and the damage of the biological components due to the degrading enzyme.

An object of the present invention is to provide a preserving agent for preserving a biological component, excellent in stability during preservation and transport and enabling the biological component to be easily recovered by a simple operation in recovering. Another object of the present invention is to provide a hydrogel capable of being suitably used as the preserving agent and a modified hyaluronic acid capable of being suitably used in the preserving agent. Still another object of the present invention is to provide a kit for using the preserving agent. Still another object of the present invention is to provide a mixture in which a biological component is included with good preservative quality.

Solution to Problem

Thus, an aspect of the present invention relates to an agent for preserving a biological component, comprising a hydrogel. In the preserving agent, the hydrogel comprises a crosslinked product formed from a compound having a plurality of hydroxyl groups and a modified hyaluronic acid having substituents capable of reacting with the hydroxyl groups to form a crosslinked structure. By using the preserving agent, the stability of a biological component during preservation becomes excellent and the biological component can be easily recovered by a simple operation.

In one embodiment, the substituents may each be a dihydroxyboryl group.

In one embodiment, the modified hyaluronic acid may have disaccharide units represented by the following formula (1):

[Chemical Formula 1]

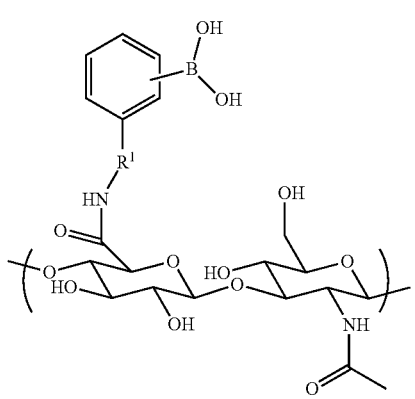

(1)

wherein $R^1$ represents a direct bond or a divalent group.

In one embodiment, the hydrogel may further comprise unmodified hyaluronic acid.

In one embodiment, the hydrogel may further comprise at least one selected from a medium for cells and a physiological buffer.

In one embodiment, the biological component may comprise at least one selected from cells, a 2-dimensional or 3-dimensional cellular aggregate constructed from cells, and a tissue or organ of biological origin.

One aspect of the present invention relates to a hydrogel comprising a crosslinked product formed from a modified hyaluronic acid having disaccharide units represented by the following formula (1):

[Chemical Formula 2]

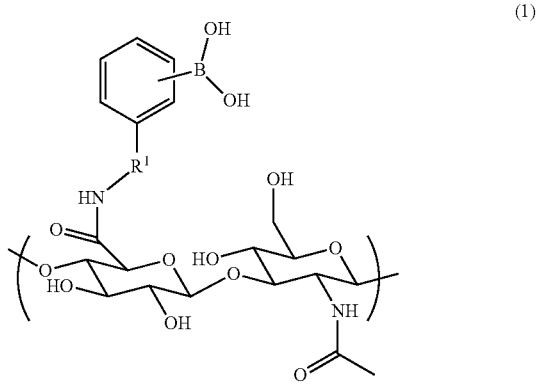

(1)

wherein $R^1$ represents a direct bond or a divalent group, and a compound having a plurality of hydroxyl groups capable of reacting with the disaccharide units to form a crosslinked structure.

One aspect of the present invention also relates to a mixture comprising a hydrogel and a biological component embedded in the hydrogel. In the mixture, the hydrogel comprises a crosslinked product formed from a compound having a plurality of hydroxyl groups and a modified hyaluronic acid having substituents capable of reacting with the hydroxyl groups to form a crosslinked structure.

One aspect of the present invention also relates to a modified hyaluronic acid having disaccharide units represented by the following formula (1):

[Chemical Formula 3]

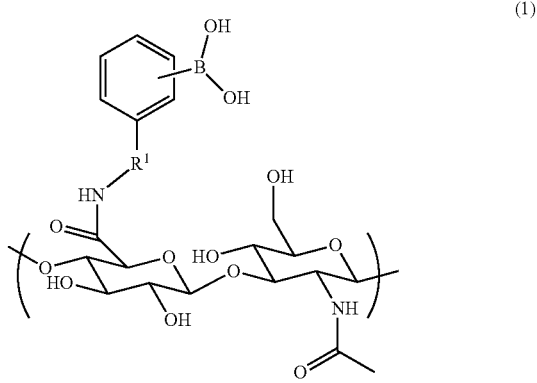

(1)

wherein $R^1$ represents a direct bond or a divalent group.

One aspect of the present invention also relates to a kit for preparing an agent for preserving a biological component. The kit comprises a first agent containing a compound having a plurality of hydroxyl groups and a second agent containing a modified hyaluronic acid having substituents capable of reacting with the hydroxyl groups to form a crosslinked structure.

One aspect of the present invention also relates to a production method for producing the mixture. The production method comprises a step of mixing the compound, the modified hyaluronic acid, and the biological component to form a hydrogel while embedding the biological component in the hydrogel.

In addition, one aspect of the present invention relates to a recovery method for recovering a biological component from the mixture. The recovery method comprises a step of dissociating at least a portion of the crosslinked structure of the crosslinked product to water-solubilize the hydrogel.

Advantageous Effects of Invention

According to the present invention, an agent for preserving a biological component can be provided which is excellent in stability during preservation and transport and enables the biological component to be easily recovered by a simple operation in recovering. According to the present invention, a hydrogel capable of suitably used as the preserving agent, a modified hyaluronic acid capable of being suitably used in the preserving agent, and a kit for using the preserving agent can also be provided. In addition, according to the present invention, a mixture can be provided in which a biological component is included with good preservative quality.

DESCRIPTION OF EMBODIMENTS

Figure 1:
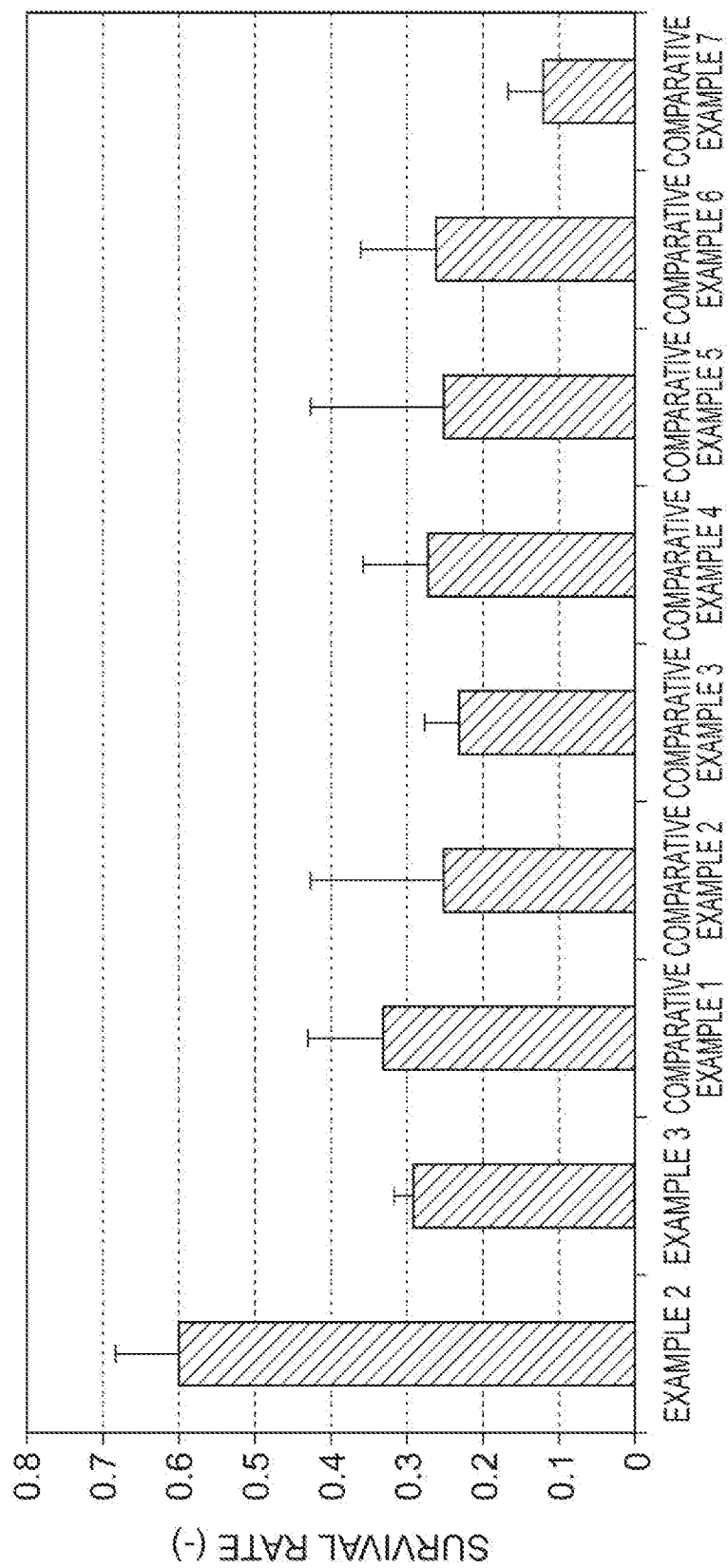
FIG. 1 is a graph showing the survival rate of cells (mouse ES cells) at day 5 of chilled preservation in Examples 2 to 3 and Comparative Examples 1 to 7.

One preferred embodiment of the present invention will be described below.

The agent for preserving a biological component according to the present embodiment is a preserving agent for preserving a biological component and comprises a hydrogel for embedding the biological component.

The hydrogel of the present embodiment comprises a crosslinked product for lied from a compound having a plurality of hydroxyl groups and a modified hyaluronic acid having substituents capable of reacting with the hydroxyl groups to form a crosslinked structure. In other words, the hydrogel of the present embodiment comprises a crosslinked substance in which the modified hyaluronic acid is crosslinked with the compound. The preserving agent according to the present embodiment can acquire excellent preservation stability by the embedding of a biological component using such a hydrogel.

Hyaluronic acid is a water-soluble macromolecular polysaccharide universally present in a living body, for example, as the main component of the synovial fluid or vitreous body of vertebrates. The modified hyaluronic acid is hyaluronic acid modified in such a way that it has the substituents, and the hydrogel achieves high biocompatibility by having a crosslinked product formed using the modified hyaluronic acid. CD44 as a receptor binding to hyaluronic acid exists on the cell surface, and the stimulation of cells by the binding and the high water-holding capacity of hyaluronic acid are expected to contribute to the stabilization of a biological component.

The crosslinked product has a rigid macromolecular chain derived from the modified hyaluronic acid. Thus, the hydrogel comprising the crosslinked product is excellent in the capacity of retaining a biological component and can sufficiently protect the biological component from damage during transport, such as oscillation.

In addition, the modified hyaluronic acid can be easily dissolved in an aqueous solvent since it has the hyaluronic acid-derived macromolecular chain. Thus, the preserving agent enables the biological component held in the crosslinked product to be easily recovered by the water solubilization of the modified hyaluronic acid by the dissociation of the crosslinked structure of the crosslinked product.

(1) Modified Hyaluronic Acid

The modified hyaluronic acid has a hyaluronic acid-derived polysaccharide macromolecular chain (hereinafter sometimes referred to as "hyaluronic acid sugar chain"), and has substituents capable of reacting with hydroxyl groups to form a crosslinked structure.

The modified hyaluronic acid can be obtained, for example, by adding side chains having the substituents to hyaluronic acid (raw material hyaluronic acid). Hyaluronic acid is a linear macromolecular polysaccharide in which β-D-N-acetylglucosamine and β-D-glucuronic acid are alternately bound. Hyaluronic acid may be obtained by any production method/acquisition method, and may be, for example, extracted from animal tissue or produced by a fermentation method.

The molecular weight or the like of raw material hyaluronic acid is not particularly limited. The weight average molecular weight Mw of raw material hyaluronic acid may be, for example, 5000 to 4000000, 20000 to 800000, or 50000 to 400000. The weight average molecular weight within the above range can reduce the solution viscosity to a low level thereby to reduce risk of damaging cells by shear stress during stirring for gelation, resulting in enabling the survival rate of the cells to be effectively increased. The polydispersity (the ratio of the number average molecular weight Mn to the weight average molecular weight Mw (Mw/Mn)) of raw material hyaluronic acid may be, for example, 1 to 10, 1 to 2, or 1.4 to 2.

The substituents which the modified hyaluronic acid has are groups capable of reacting with hydroxyl groups to form a crosslinked structure. A dihydroxyboryl group ($-B(OH)_2$) is preferable as the substituent in view of easy availability, high safety, and easy recovery of a biological component.

The modified hyaluronic acid having dihydroxyboryl groups as the substituents can form a hydrogel by easily crosslinking with a compound having a plurality of hydroxyl groups. In the crosslinked product formed from the modified hyaluronic acid, a crosslinked structure is probably formed by the covalent bonding or coordinate bonding between boron atoms of dihydroxyboryl groups and oxygen atoms of hydroxyl groups, and the crosslinked structure can easily be dissociated by adding a compound having oxygen atoms capable of binding to a boron atom (for example, a sugar alcohol such as sorbitol) in place of oxygen atoms derived from the compound having a plurality of hydroxyl groups thereby to water-solubilize. In other words, the use of the modified hyaluronic acid makes easier the water solubilization of the crosslinked product through the dissociation, enabling the easier recovery of a biological component.

Examples of the substituent include aromatic boryl groups including a dihydroxyborylphenyl group, a dihydroxyborylnaphtyl group, a dihydroxyborylanthracenyl group, and their derivatives, and aliphatic boryl groups including alkylboryl groups and their derivatives. Among these, in view of more improving the preservation stability of a biological component, aromatic boryl groups are preferable and a dihydroxyphenyl group is more preferable.

The substituent may directly bind to the hyaluronic acid sugar chain or may bind thereto through a linker.

The linker is not particularly limited, and may be, for example, one having amide bond, ester bond, or ether bond. It is desirable that the linker be a structure difficult to be dissociated during the preservation of a biological component and during the recovery of a biological component, and in view thereof, it is preferable that it be one having amide bond. It is preferable that the linker consist of any of carbon, hydrogen, nitrogen, and oxygen atoms, and it is also preferable that the linker consist of one or more constitutional units selected from the group consisting of amide bond, ether bond, lower alkyl groups (alkyl groups having 4 or less carbon atoms), lower alkylene groups (alkylene groups having 4 or less carbon atoms), and a hydroxyl group.

The method for introducing the substituent into the hyaluronic acid sugar chain is not particularly limited.

For example, the substituent can be introduced by reacting a compound having a group having a carbon-carbon double bond, such as a vinyl group or an allyl group, as a polymerizable group and having the substituent with hyaluronic acid into which a polymerizable group is introduced.

Examples of the compound having a polymerizable group include p-vinylphenylboronic acid, m-vinylphenylboronic acid, p-(meth)acryloyloxyphenylboronic acid, m-(meth)acryloyloxyphenylboronic acid, p-(meth)acrylamidophenylboronic acid, p-vinyloxyphenylboronic acid, m-vinyloxyphenylboronic acid, and vinyl urethane phenylboronic acid; among these, p-vinylphenylboronic acid and m-vinylphenylboronic acid can suitably be used.

The hyaluronic acid having a polymerizable group can be obtained, for example, by reacting a compound having an amino group and a polymerizable group with hyaluronic acid. Hyaluronic acid, which has carboxyl groups, can react with the amino group of the compound to form amide bond for the easy introduction of the polymerizable group into hyaluronic acid. The reaction of the compound with hyaluronic acid can be conducted using, for example, 1-ethyl-3-(3-dimethylaminopropyl)carbodiimide hydrochloride and N-hydroxysuccinimide as reaction reagents.

Examples of the compound having an amino group and a polymerizable group include allylamine and propargylamine.

In addition, for example, a compound having an amino group and the substituent can be reacted with hyaluronic acid to introduce the substituent into the hyaluronic acid sugar chain. The reaction can be conducted using, for example, 1-ethyl-3-(3-dimethylaminopropyl)carbodiimide hydrochloride and N-hydroxysuccinimide as reaction reagents, as described above.

Examples of the compound having an amino group and the substituent include aminophenylboronic acid, 2-aminoethylcarbamoylphenylboronic acid, and 3-aminopropylcarbamoylphenylboronic acid.

It is preferable that the modified hyaluronic acid of the present embodiment be one having disaccharide units represented by the following formula (1). The use of the modified hyaluronic acid provides a crosslinked product more excellent in the preservation stability of a biological component. In the crosslinked product formed from the modified hyaluronic acid, the crosslinked structure can be easily dissociated, making easier the recovery of a biological component.

[Chemical Formula 4]

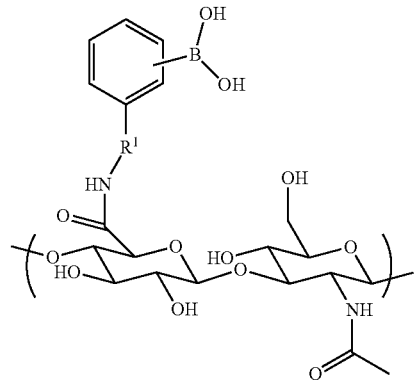

(1)

In the formula, $R^1$ represents a direct bond or a divalent group. "$R^1$ represents a direct bond" indicates that the nitrogen atom binding to $R^1$ directly binds to the carbon atom in the benzene ring, binding to $R^1$.

It is preferable that $R^1$ binds to the meta position or para position of the phenylboronic acid residue.

Examples of the divalent group in $R^1$ include an alkylene group, an amide group, an alkyleneoxy group, and a group constructed of a combination of these groups.

Examples of the divalent group in $R^1$ include a group represented by the following formula (2):

$$-CH_2CH_2-(CH_2)_m-(OCH_2CH_2)_n-(CH_2)_m-NH-CO- \quad (2)$$

The nitrogen atom in the hyaluronic acid sugar chain binds to the left end in the formula (2), and the carbon atom in the benzene ring binds to the right end.

In the formula, m represents an integer of 0 or 1, and n represents an integer of 0 to 3.

The modified hyaluronic acid may be one in which some of the carboxyl groups in the hyaluronic acid sugar chain of raw material hyaluronic acid are modified by groups having the substituents. A modification rate by the substituent is preferably 2% or more, more preferably 5% or more, still more preferably 10% or more. The modification rate of 2% or more results in the denser formation of the crosslinked structure and thus tends to make better the preservation stability of a biological component.

The modification rate by the substituent may be 50% or less, preferably 30% or less, more preferably 25% or less, still more preferably 20% or less. The modification rate of more than 50% does not tend to improve the preservation stability of a biological component. The modification rate of 50% or less tends to more facilitate the recovery of a biological component owing to the dissociation of the crosslinked structure.

The modification rate by the substituent in the modified hyaluronic acid herein indicates a value calculated according to the following equation:

> Modification rate(%)=the amount(mole) of the substituents in the modified hyaluronic acid/(the amount(mole) of the substituents in the modified hyaluronic acid+the amount(mole) of hyaluronic acid-derived carboxyl groups in the modified hyaluronic acid)

The amount of the carboxyl groups in the modified hyaluronic acid can be measured by the following carbazole-sulfuric acid method.

(Carbazole-Sulfuric Acid Method)

Dry modified hyaluronic acid powder is completely dissolved in distilled water to a concentration of 0.03 to 0.1% (w/v). 40 μL of the resultant modified hyaluronic acid solution is placed in a microtube, and 200 μL of boric acid-sulfuric acid reagent (0.95 g of sodium tetraborate decahydrate is weighed and added to 100 mL of sulfuric acid, which is then stirred for 4 hours or more using a stirrer device for dissolution) is added thereto, which is then stirred with a vortex, followed by heating the resultant with a heat block at about 100° C. Immediately after 30 minutes, the resultant is taken out, cooled in ice-cold water, and returned to room temperature. 10 μL of carbazole reagent (a 95% ethanol solution having a carbazole concentration of 1.25 g/L) is added thereto, which is then stirred with a vortex, followed by heating the resultant with a heat block at about 100° C. Immediately after 15 minutes, the resultant is taken out, cooled in ice-cold water, and returned to room temperature. 100 μL of the resultant each sample is placed in a 96-well plate, and measured for absorbance at a wavelength of 530 nm using a microplate reader (VERSAmax, Molecular Devices Japan K.K.).

At this time, a D-glucuronolactone aqueous solution is used as a standard solution. 0.500 g of D-glucuronolactone is precisely measured into a 100-mL measuring flask, dissolved in water, and then adjusted to make a standard stock solution. The standard stock solution is diluted with distilled water to prepare 2.5 μg/mL, 10 μg/mL, and 40 μg/mL solutions. Using these solutions, calibration curve data of absorbance are obtained, and the amount (concentration) of hyaluronic acid in the unmodified moiety is calculated. The coefficient for converting the D-glucuronolactone amount (concentration) to the hyaluronic acid amount (concentration) is set to 2.279. From the hyaluronic acid amount in the unmodified moiety measured here, the amount (mole) of hyaluronic acid-derived carboxyl groups in the modified hyaluronic acid is calculated according to the following equation:

> The amount(mole) of hyaluronic acid-derived carboxyl groups in the modified hyaluronic acid=the hyaluronic acid amount(g) in the unmodified moiety measured/398(the molecular weight of the disaccharide unit of hyaluronic acid)

The amount of the substituent in the modified hyaluronic acid can be properly changed according to the type of the substituent. For example, when the substituent is a group having a dihydroxyboryl group, measurement can be carried out by the following atomic absorption method.

(Atomic Absorption Method)

Dry modified hyaluronic acid powder is dissolved in distilled water. A solution in which 0.3 mL of the modified hyaluronic acid solution is mixed with 0.3 mL of a 0.2 N sodium hydroxide solution is used as a measurement sample. A pyrolytic tube is installed in an atomic absorption measurement device (A-6800 from Shimadzu Corporation), and the program shown in the following Table 1 is set. 20 μL of the measurement sample is placed and measured in a measuring location. The program RAMP means that the temperature is raised at a constant gradient for a set time until a target temperature is achieved, and STEP means that the temperature is immediately raised until a target temperature is achieved.

In this measurement, a boron standard solution (1000 ppm, Wako Pure Chemical Industries Ltd.) is used and diluted with distilled water, and its solutions adjusted to concentrations of 0.5 μg/mL, 1.0 μg/mL, 1.6 μg/mL, 2.0 μg/mL, and 2.5 μg/mL are used as standard solutions. Distilled water is used for 0 μg/mL. Like the modified hyaluronic acid solution, these solutions are mixed with an equal volume of a 0.2 N sodium hydroxide solution and measured for the boron amount using the atomic absorption measurement device. Calibration curve data are obtained from the measurement results to calculate the boron atom amount (that is, the dihydroboryl group amount) (mole).

TABLE 1

| Temperature (° C.) | Time (second) | Heating Condition | Gas Flow Rate (L/min) |
|---|---|---|---|
| 150 | 20 | RAMP | 0.1 |
| 250 | 10 | RAMP | 0.1 |
| 900 | 10 | RAMP | 1 |
| 900 | 10 | STEP | 1 |
| 900 | 3 | STEP | 0 |
| 2750 | 2 | STEP | 0 |
| 2750 | 1 | STEP | 1 |

(2) Compound Having Plurality of Hydroxyl Groups

The compound having a plurality of hydroxyl groups can be used without particular limitation, provided that it is a compound capable of forming a crosslinked structure with the modified hyaluronic acid to form a hydrogel. For example, the molecular weight, saponification degree, and the like of the compound are not particularly limited.

It is preferable that the compound be a water-soluble macromolecule. The crosslinked product formed from the water-soluble macromolecule can be easily water-solubilized by the dissociation of the crosslinked structure, and the water-soluble macromolecule and the modified hyaluronic acid after water-solubilizing can be easily washed away with an aqueous solvent. Thus, when the compound is a water-soluble macromolecule, the recovery of a biological component is easier.

It is also preferable that the compound be a polymer whose aqueous solution has a pH ranging from 6.0 to 8.0. Such a polymer more improves the preservation stability of a biological component.

The compound may be a polymer whose main chain directly binds to hydroxyl groups, or may be a polymer which has hydroxyl groups on the side chains binding to the main chain.

Examples of the compound include olefin polymers having hydroxyl groups, such as polyvinyl alcohol, styrene polymers having hydroxyl groups, and polyester polymers having hydroxyl groups. Among these, olefin polymers having hydroxyl groups are preferable and polyvinyl alcohol is most preferable.

As the compound, a polymer having a polysaccharide macromolecular chain can also be used. A polysaccharide macromolecule, which has a plurality of hydroxyl groups on the main chain, hardly forms a hydrogel because of the rigidity of the main chain. Thus, as the compound, a polysaccharide macromolecule can suitably be used which is modified with a group containing a plurality of hydroxyl groups so that it can form a hydrogel with the modified hyaluronic acid. Examples of the group containing a plurality of hydroxyl groups include groups having structures derived from monosaccharides, disaccharides, polyhydric alcohols having a 1,2-diol structure, glycerin, polyvinyl alcohol, and the like.

(3) Other Component

The preserving agent according to the present embodiment may comprise components other than the hydrogel, and the hydrogel may comprise components other than the crosslinked product.

The hydrogel is formed, for example, by comprising the crosslinked product and an aqueous solution. It is preferable that the pH of the aqueous solution be in the range of 6.0 to 8.0, in view of reliably obtaining the preservation stability of a biological component. It is also preferable that the osmotic pressure of the aqueous solution be 200 to 400 mOsm/kg.

The hydrogel may comprise a cellular medium, a physiological buffer, or the like as the aqueous solution. The cellular medium is used to give a sufficient amount of nutrient when cells are grown in an artificial environment, and the use of the hydrogel comprising the cellular medium more improves the preservation stability of biological components (particularly, various cells). The composition of the cellular medium can be properly changed depending on the object to be preserved; however, it is preferable that the composition comprise saccharides and inorganic salts. The cellular medium may also comprise amino acids, lipids, vitamins, serum, and the like.

The physiological buffer may contain, for example, sodium ion, potassium ion, magnesium ion, calcium ion, phosphate ion, carbonate ion, and hydrogencarbonate ion. As the physiological buffer, phosphate buffered saline (PBS) can suitably be used.

The preserving agent according to the present embodiment may further comprise unmodified hyaluronic acid. The hydrogel has biocompatibility due to the hyaluronic acid sugar chain of the modified hyaluronic acid; however, when the crosslinked structure is tightly formed in a portion of the hydrogel, the biocompatibility due to the hyaluronic acid sugar chain may not sufficiently be exhibited in the portion. In this regard, the addition of unmodified hyaluronic acid to the preserving agent provides sufficient biocompatibility even in the vicinity of the tightly formed crosslinked structure and can more improve the preservation stability of a biological component.

The unmodified hyaluronic acid can be properly added, for example, in the range in which it is dissolved in an aqueous solvent. The content of the unmodified hyaluronic acid may be, for example, 0.01% by mass to 20% by mass, preferably 0.01 to 10% by mass based on the total amount of the preserving agent.

The preserving agent according to the present embodiment may further comprise, in addition to the abovementioned, for example, a reducing agent (glutathione, vitamin C, or the like), a cell death-suppressing agent (c-AMP or the like), and a growth factor (HGF, bFGF, or the like).

The hydrogel of the present embodiment preferably has an elastic modulus of 0.001 to 10000 Pa, more preferably 0.01 to 1000 Pa. The loss elastic modulus of the hydrogel is preferably 0.001 to 10000 Pa, more preferably 0.01 to 1000 Pa. The loss elastic modulus and the elastic modulus of the hydrogel herein each indicate a value measured by a method as described in Example.

The object to be preserved using the preserving agent according to the present embodiment is not particularly limited provided that it is a biological component. Examples of the biological component to be preserved include cells (stem cells, such as ES cells or iPS cells, progenitor cells, mature cells, or the like), germ cells, genetically-modified cells, or a 2-dimensional or 3-dimensional cellular aggregate (tissue-like structure) constructed from them alone or a plurality of types of cells, a biotissue, and an organ.

The hydrogel according to the present embodiment can be formed, for example, by mixing an aqueous solution containing the compound having a plurality of hydroxyl groups (hereinafter sometimes referred to as a compound solution) with an aqueous solution containing the modified hyaluronic acid (hereinafter sometimes referred to as a modified hyaluronic acid solution).

According to the preserving agent in accordance with the present embodiment, a biological component can be stably preserved by embedding the biological component in the hydrogel of the preserving agent. The method for embedding a biological component is not particularly limited.

In the present embodiment, the biological component preserved in the preserving agent can also be obtained, for example, by a method which involves forming the hydrogel in an aqueous solution containing the biological component to embed the biological component in the hydrogel. At this time, the temperature in forming the hydrogel is preferably 0 to 37° C., more preferably 4 to 37° C. to avoid a deleterious effect on the biological component.

An example of the method is as follows: a biological component is dispersed in one of the modified hyaluronic acid solution and the compound solution in advance, and the other is added to the dispersion to form a hydrogel.

In the present embodiment, the biological component preserved in the preserving agent can easily be recovered by dissociating at least a part of the crosslinked structure of the crosslinked product. That is, the recovery method according to the present embodiment is a method for recovering the biological component embedded in the hydrogel, and comprises a step of dissociating at least a part of the crosslinked structure of the crosslinked product to water-solubilize the hydrogel.

The method for dissociating the crosslinked structure of the crosslinked product can be properly selected depending on the formed crosslinked structure. For example, when the modified hyaluronic acid has a dihydroxyboryl group as the substituent, the crosslinked structure is formed by the covalent bond or coordinate bond between the boron atom of the dihydroxyboryl group and the oxygen atom of the hydroxyl group. In this case, the addition of a compound (hereinafter referred to as a compound for recovery) having an oxygen atom capable of binding to the boron atom in place of the oxygen atom derived from the polymer enables the easy dissociation of the crosslinked structure.

The compound for recovery is a compound containing an oxygen atom capable of binding to the boron atom through covalent bond or coordinate bond, preferably a compound having a hydroxyl group. It is preferable that the compound for recovery be a water-soluble compound in view of its ability to be easily washed away with an aqueous solvent on recovering a biological component.

The compound for recovery is a compound dissociating the crosslinked structure to water-solubilize the hydrogel, the compound being a compound containing an oxygen atom capable of binding to the boron atom through covalent bond or coordinate bond, preferably a compound having a hydroxyl group. It is preferable that the compound for recovery be a water-soluble compound in view of its ability to be easily washed away with an aqueous solvent on recovering a biological component.

Examples of the compound for recovery include monosaccharides, disaccharides, sugar alcohols (for example, sorbitol), oligosaccharides, and low-molecular weight polyhydric alcohols, such as glycerin.

In the present embodiment, the preserving agent described above may be directly provided as a preserving agent, or may be applied in the form of a kit for forming a preserving agent.

The preserving agent kit according to the present embodiment comprises a first agent containing the compound having a plurality of hydroxyl groups and a second agent containing the modified hyaluronic acid. The use of the kit can easily provide the preserving agent by forming a hydrogel from the first agent and the second agent.

In the preserving agent kit, the first agent may be one containing the compound as a solid component, or may be an aqueous solution containing the compound. The second agent may be one containing the modified hyaluronic acid as a solid component, or may be an aqueous solution containing the modified hyaluronic acid. In addition, the first agent and the second agent may contain the above-described components (for example, unmodified hyaluronic acid) in addition to the compound and the modified hyaluronic acid.

Preferred embodiments of the present invention have been described above, but the present invention is not limited to the embodiments.

For example, in one aspect, the present invention may relate to a mixture comprising the hydrogel and a biological component embedded in the hydrogel. The present invention can also be said to be a method for producing the mixture, and can also be said to be a recovery method for recovering a biological component from the mixture.

In one aspect, the present invention may relate to the modified hyaluronic acid, and may relate to a method for producing the modified hyaluronic acid.

EXAMPLES

The present invention will be more specifically described below with reference to Examples, but the present invention is not limited to these Examples.

[Preparation of Modified Hyaluronic Acid]

Example 1

1.0 g of hyaluronic acid having a molecular weight of 50000 was placed in a flask, to which 150 mL of distilled water was then added for complete dissolution. After adding 75 mL of 1,4-dioxane, 0.54 g of m-aminophenylboronic acid (from Wako Pure Chemical Industries Ltd.) was added. After stirring at room temperature for 2 hours, 1.2 g of 1-ethyl-3-(3-dimethylaminopropyl)cabodiimide hydrochloride (from Nacalai Tesque Co., Ltd.) and 0.7 g of N-hydroxysuccinimide (Nacalai Tesque Co., Ltd.) were added, followed by stirring at room temperature for 12 hours. A 5 M sodium bicarbonate solution was dropwise added so that the pH of the reaction solution is 8.5 or more, followed by stirring a whole day and night. 4.5 g of sodium chloride was added to the reaction solution, and after dissolution, 225 mL of acetone was gradually poured to precipitate a modified hyaluronic acid. The operation of removing the supernatant by decantation, pouring 100 mL of 80% acetone diluted with distilled water, and stirring the resultant for 1 hour was carried out 3 times. Then, the operation of adding 100 mL of acetone and stirring the resultant for 1 hour was carried out 3 times. The precipitate was recovered and air-dried under conditions of reduced pressure. The modified hyaluronic acid was dissolved in distilled water and measured for the modification rate; as a result, the modification rate was found to be 11.4 mol %.

[Embedding, Preservation, and Recovery of Mouse ES Cells Using Modified Hyaluronic Acid]

Example 2

The cells used were mouse ES cells (EB5). Polyvinyl alcohol (JF-17 from Japan Vam & Poval Co., Ltd.) and unmodified hyaluronic acid having a molecular weight of 50000 were dissolved in potassium phosphate buffer (pH 6.8) to final concentrations of 1.0% (solution A). 0.2 mL of solution A was placed in each well of a 48-well plate for culture and the solution was made uniform on the well bottom. Cells at day 2 of culture were treated with trypsin to recover the cells from the culture dish; the modified hyaluronic acid prepared in Example 1, having an introduction rate of 11.4 mol % was dissolved in potassium phosphate buffer (pH 6.8) to make a solution having a final concentration of 1.0% (solution B); and 0.2 mL of the solution was placed in each of the wells and stirred to form a hydrogel. The hydrogel was preserved in refrigeration (about 4° C.) for 5 days after its formation.

After 5 days of preservation, sorbitol-containing saline (sorbitol concentration: 10 mg/ml, addition amount: 1 ml) was added to each well, and the gel was dissolved by pipetting. The liquid after dissolution was placed in a microtube and centrifuged to recover the cells. After removing the supernatant, an adequate amount of a trypan blue solution was added to the cells to evaluate the cell survival rate, and life or death was determined based on the difference of dyeability.

The survival rate of cells was calculated according to the following equation:

Cell survival rate(−)=(the counted number of live cells in the total cells)/(the counted number of the total cells)

Example 3

The embedding, preservation, and recovery of cells were carried out in the same way as in Example 2 except for removing unmodified hyaluronic acid from solution A.

Comparative Example 1

The embedding, preservation, and recovery of cells were carried out in the same way as in Example 2 except for removing the modified hyaluronic acid from solution B.

Comparative Example 2

The embedding, preservation, and recovery of cells were carried out in the same way as in Example 2 except for removing polyvinyl alcohol from solution A.

Comparative Example 3

The embedding, preservation, and recovery of cells were carried out in the same way as in Example 2 except for removing unmodified hyaluronic acid from solution A and removing the modified hyaluronic acid from solution B.

Comparative Example 4

The embedding, preservation, and recovery of cells were carried out in the same way as in Example 2 except for removing polyvinyl alcohol from solution A and removing the modified hyaluronic acid from solution B.

Comparative Example 5

The embedding, preservation, and recovery of cells were carried out in the same way as in Example 2 except for removing polyvinyl alcohol and unmodified hyaluronic acid from solution A.

Comparative Example 6

The embedding, preservation, and recovery of cells were carried out in the same way as in Example 2 except for removing polyvinyl alcohol and unmodified hyaluronic acid from solution A and removing the modified hyaluronic acid from solution B.

The compositions of the solution A and the solution B according to Examples 2 to 3 and Comparative Examples 1 to 6 are shown in Table 2. In the table, + indicates containing the appropriate component, and – indicates not containing the appropriate component.

TABLE 2

|  | Solution A | | Solution B Modified |
| --- | --- | --- | --- |
|  | Polyvinyl Alcohol | Unmodified Hyaluronic Acid | Hyaluronic Acid |
| Example 2 | + | + | + |
| Example 3 | + | – | + |
| Comparative Example 1 | + | + | – |
| Comparative Example 2 | – | + | + |
| Comparative Example 3 | + | – | – |
| Comparative Example 4 | – | + | – |
| Comparative Example 5 | – | – | + |
| Comparative Example 6 | – | – | – |

Comparative Example 7

10 mg of thiol-modified hyaluronic acid (HyStem; Glycosan BioSystems) was dissolved in 1.0 mL of phosphate buffered saline. 2.5 mg of a crosslinking initiator (Extralink; Glycosan BioSystems) was dissolved in 0.25 mL of distilled water. Mouse ES cells (EB5) at day 2 of culture were suspended to a final concentration of $1.0 \times 10^6$ cells/mL in 1.0 mL of the thiol-modified hyaluronic acid solution, and 0.25 mL of the crosslinking initiator solution was then mixed therewith, which was immediately dispensed in amounts of 0.4 mL in a 48-well plate and allowed to stand at room temperature for 30 minutes to provide a gel. The gel was preserved in refrigeration (about 4° C.) for 5 days.

After preservation, 1.0 mL of a solution in which hyaluronidase (Hyaluronidase from bovine testes (Type IV), Sigma) was dissolved in a 10 mM acetic acid-sodium acetate solution (pH 5.7) and adjusted to a concentration of 2000 units/mL was added thereto, which was then maintained at 37° C. for about 30 minutes. The dissolved liquid was recovered into a microtube; the cells were recovered by centrifugation; after removing the supernatant, 1.0 mL of phosphate buffered saline was added; after slight stirring, centrifugation was again carried out; and only the supernatant was carefully removed to recover the cells. The survival rate of the cells was evaluated.

The cell survival rate in Examples 2 to 3 and Comparative Examples 1 to 7 are shown in FIG. 1.

[Solubility Test of Hydrogel]

Example 4

Figure 2:
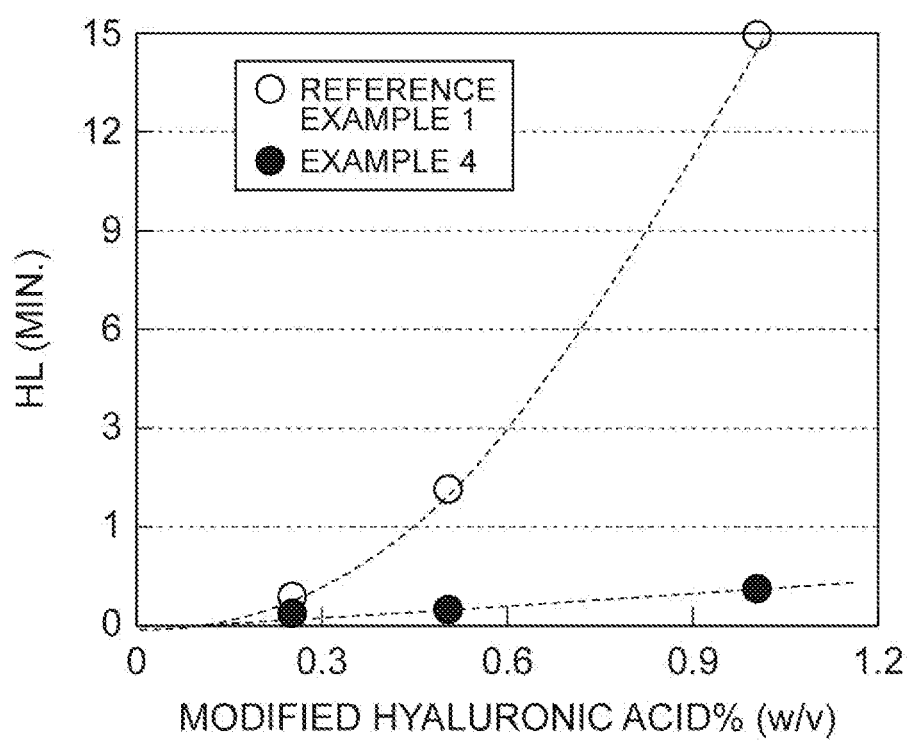
FIG. 2 is a graph showing the dissolution of a mixed gel by using a sorbitol solution.

Aminophenylboronic acid-modified hyaluronic acid having a modification rate of 11 mol % and a molecular weight of about 2000000 was dissolved in physiological phosphate buffer and adjusted to concentrations of 0.5, 1.0, and 2.0% (w/v). 0.2 mL of each concentration of the modified hyaluronic acid solution was mixed with 0.2 mL of polyvinyl alcohol to prepare a hydrogel. The hydrogel was poured into 9.6 mL of saline or 10 mg/mL sorbitol-containing saline and dissolved while stirring with a stirrer at room temperature. The supernatant was recovered in amounts of 0.2 mL several times with time. The amount of hyaluronic acid in the recovered solution was measured by the above-described carbazole-sulfuric acid method to calculate the concentration of hyaluronic acid in the supernatant. The gel solubility was calculated using the following equation:

Gel Solubility=the concentration(%) of hyaluronic acid in the supernatant/the hyaluronic acid concentration(%) after complete dissolution Time taken for the solubility to reach 50% (HL50) was determined from the dissolution behavior of each gel; the relationship between the concentration of the modified hyaluronic acid in the hydrogel and HL50 is shown in FIG. 2.

Reference Example 1

HL50 was determined in the same way as in Example 4 except for using sorbitol-free saline in place of sorbitol-containing saline. The relationship between the concentration of the modified hyaluronic acid in the hydrogel and HL50 is as shown in FIG. 2.

From the results shown in FIG. 2, it was confirmed that the hydrogel according to the present invention can be easily dissolved by adding a suitable compound for recovery while sufficiently suppressing water solubilization due to saline or the like during preservation.

[Viscoelasticity Measurement of Hydrogel]

Example 5

Aminophenylboronic acid-modified hyaluronic acid having a modification rate of 11 mol % was prepared and dissolved to a concentration of 1% (w/v) in phosphate-buffered saline to make a measurement sample. Polyvinyl alcohol was adjusted to a concentration of 1% (w/v) using phosphate-buffered saline to make a measurement sample. The 1% (w/v) modified hyaluronic acid solution and the 1% (w/v) polyvinyl alcohol solution were mixed in equal amounts to prepare a measurement sample having a hydrogel concentration of 1% (w/v).

Viscoelasticity was measured using a rheometer (MCR300 Rheometer, Anton Paar Co., Ltd.) fitted with a jig (CP50-1). About 1.0 mL of each measurement sample was placed on the stage and measured at an amplitude of 3%, a frequency of 0.01 to 10 Hz, and a temperature of 37° C. Among the measurement results, the elastic modulus at a frequency of 10 Hz was $1.3 \times 10^{-6}$ Pa for the modified hyaluronic acid, 0.7 Pa for polyvinyl alcohol, and 28.1 Pa for the hydrogel, and the loss elastic modulus was 1.4 Pa for the modified hyaluronic acid, 0.1 Pa for polyvinyl alcohol, and 7.4 Pa for the hydrogel.

[Embedding, Preservation, and Recovery of Human iPS Cell Using Modified Hyaluronic Acid]

Example 6

The cells used were human iPS cells (253G1). Polyvinyl alcohol (JF-17 from Japan Vam & Poval Co., Ltd.) and unmodified hyaluronic acid having a molecular weight of 50000 were dissolved to final concentrations of 1.0% and 3.0%, respectively, in potassium phosphate buffer (pH 6.8) (solution A). The modified hyaluronic acid prepared in Example 1, having a modification rate of 11.4 mol % was dissolved in potassium phosphate buffer (pH 6.8) to make a solution having a final concentration of 3.0% (solution B). MEF cells were seeded in a 6-well plate for culture and cultured overnight, followed by seeding human iPS cells. These cells were cultured on an "as is" basis for 3 days, and solution B was poured in 1.0 mL portions for harmonization. Subsequently, solution A was poured thereinto in 1.0 mL portions, which was then stirred by shaking to form a hydrogel for embedding. The hydrogel was preserved in refrigeration (about 4° C.) for 5 days after formation.

After 5 days of preservation, the hydrogel was slightly removed using an aspirator, followed by adding sorbitol-containing saline (sorbitol concentration: 10 mg/ml, addition amount: 2 ml) into the well and allowing the resultant to stand for about 2 minutes to dissolve the gel. The operation of removing the solution using an aspirator, again adding 2 ml of saline, and removing the resultant using an aspirator was repeated 2 times. After removing the supernatant, the remaining cell groups were stained using Stemgent Alkaline Phosphatase Staining Kit to evaluate the survivability of the cells, and the number of cell groups after preservation was counted and evaluated as the residual rate.

The residual rate of cell groups was calculated according to the following equation:

Residual rate of cell groups(-)=(the number of cell groups at day 5 of preservation)/(the number of cell groups before preservation)

Comparative Example 8

The embedding, preservation, and recovery of cells were carried out in the same way as in Example 6 except for removing polyvinyl alcohol and unmodified hyaluronic acid from solution A and removing the modified hyaluronic acid from solution B.

Comparative Example 9

The embedding, preservation, and recovery of cells were carried out in the same way as in Example 6 except for adding 2.0 mL of ThelioKeep (BioVerde) in place of solutions A and B.

Figure 3:
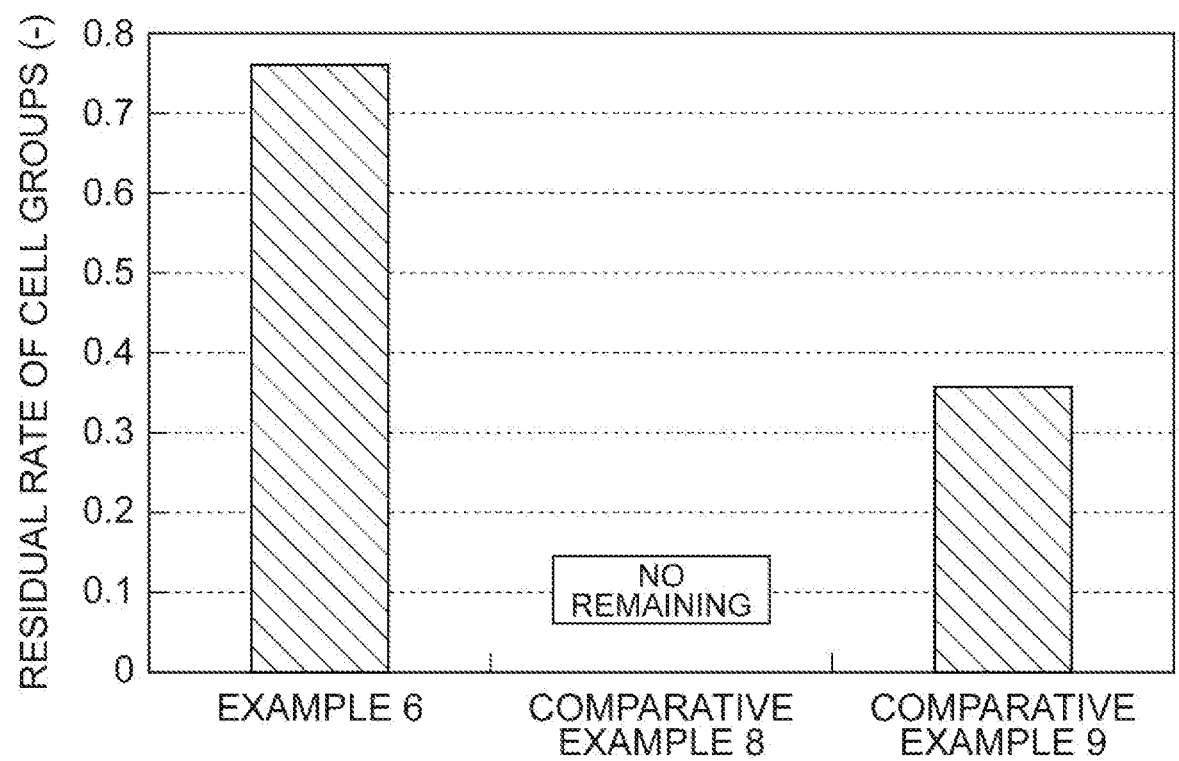
FIG. 3 is a graph showing the residual rate of cell groups (human iPS cells) at day 5 of chilled preservation in Example 6 and Comparative Examples 8 to 9.

The residual rate of cell groups in Example 6 and Comparative Examples 8 to 9 is shown in FIG. 3.

[Reduction in Oscillation Damage Using Modified Hyaluronic Acid Hydrogel]

Example 7

The cells used were mouse ES cells (EB5). Polyvinyl alcohol (JF-17 from Japan Vam & Poval Co., Ltd.) and unmodified hyaluronic acid having a molecular weight of 50000 were dissolved in potassium phosphate buffer (pH 6.8) to final concentrations of 1.0% and 3.0%, respectively (solution A). The modified hyaluronic acid prepared in Example 1, having a modification rate of 11.4 mol % was dissolved in potassium phosphate buffer (pH 6.8) to make a solution having a final concentration of 3.0% (solution B). Cells at day 2 of culture were treated with trypsin to recover the cells from the culture dish into a 15-mL conical tube. After centrifugation, the supernatant was removed, and solution B was added and suspended so that the cell concentration is $1 \times 10^6$ cells/mL. 0.5 mL of this suspension was placed in a 15-mL conical tube, to which 0.5 mL of solution A was then added, followed by carrying out vertical inversion stirring to form a hydrogel. After hydrogel formation, the hydrogel was set in a roller tube culture apparatus in a refrigerator (about 4° C.). At this time, the rotation axis direction of the roller tube culture apparatus was ensured to be horizontal and the core axis direction of the tube was ensured to be vertical to the rotation axis direction, and preservation was carried out for 5 days while performing rotation at 30 rpm.

After 5 days of preservation, sorbitol-containing saline (sorbitol concentration: 10 mg/ml, addition amount: 5.0 ml) was added to each well, and the gel was dissolved by pipetting. The liquid after dissolution was placed in a microtube and centrifuged to recover the cells. After removing the supernatant, an adequate amount of a trypan blue solution was added to the cells to evaluate the cell survival rate, and life or death was determined based on the difference of dyeability.

The survival rate of cells was evaluated in the same way as in Example 2.

Comparative Example 10

The embedding, preservation, and recovery of cells were carried out in the same way as in Example 7 except for removing polyvinyl alcohol and unmodified hyaluronic acid from solution A and removing the modified hyaluronic acid from solution B.

Comparative Example 11

The embedding, preservation, and recovery of cells were carried out in the same way as in Example 7 except for adding 1.0 mL of ThelioKeep (BioVerde) in place of solutions A and B.

Figure 4:
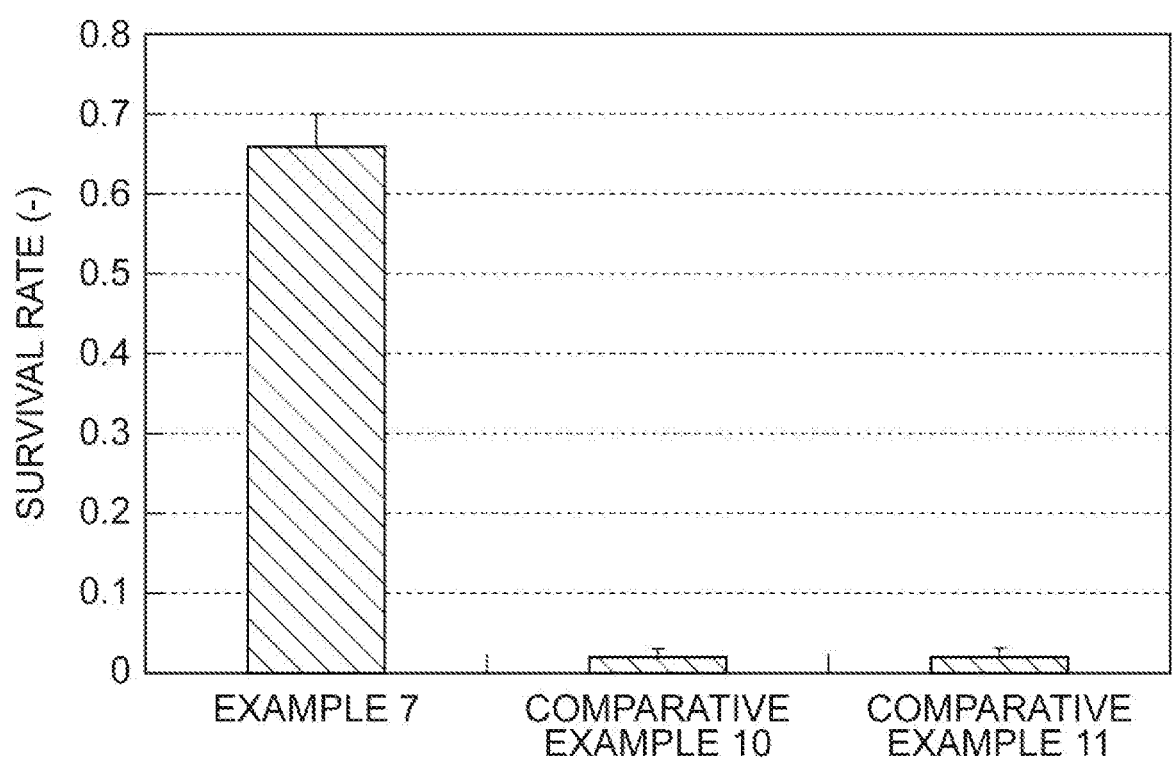
FIG. 4 is a graph showing the survival rate of cells (mouse ES cells) at day 5 of chilled preservation in Example 7 and Comparative Examples 10 to 11.

The survival rate of cells in Example 7 and Comparative Examples 10 to 11 is shown in FIG. 4.

The invention claimed is:

1. An agent for preserving a biological component, comprising a hydrogel, the hydrogel comprising a crosslinked product formed from polyvinyl alcohol and a modified hyaluronic acid having substituents capable of reacting with the hydroxyl groups to form a crosslinked structure;

wherein the modified hyaluronic acid has disaccharide units and is represented by the following formula (1):

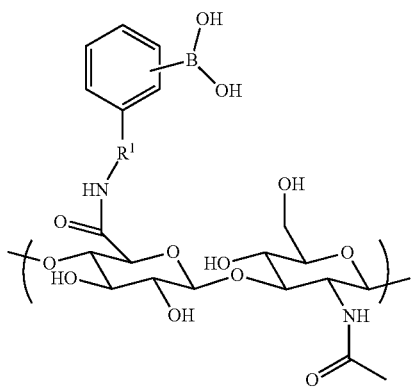

(1)

wherein R¹ represents a direct bond or a divalent group; and wherein the hydrogel further comprises unmodified hyaluronic acid.

2. The agent according to claim 1, wherein the hydrogel further comprises at least one selected from a medium for cells and a physiological buffer.

3. The agent according to claim 1, wherein the biological component comprises at least one selected from cells, a 2-dimensional or 3-dimensional cellular aggregate constructed from cells, and a tissue or organ of biological origin.

4. A kit for preparing an agent for preserving a biological component, the kit comprising a first agent containing polyvinyl alcohol and unmodified hyaluronic acid and a second agent containing a modified hyaluronic acid having substituents capable of reacting with the hydroxyl groups to form a crosslinked structure;

wherein
the modified hyaluronic acid has disaccharide units and is represented by the following formula (1):

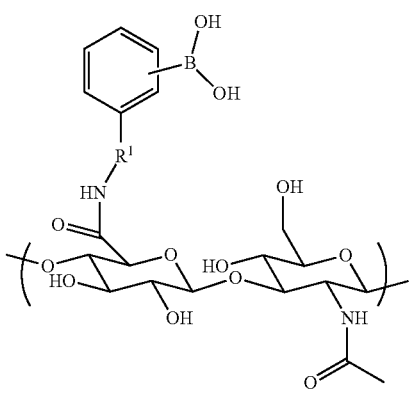

(1)

wherein R¹ represents a direct bond or a divalent group.

* * * * *